United States Patent [19]

Clack et al.

[11] 3,937,615

[45] Feb. 10, 1976

[54] AUTO-RANGING GLUCOSE MEASURING SYSTEM

[75] Inventors: Peter J. Clack, Doylestown; George R. Moreland, Green Lane, both of Pa.

[73] Assignee: Leeds & Northrup Company, North Wales, Pa.

[22] Filed: Dec. 17, 1974

[21] Appl. No.: 533,553

[52] U.S. Cl. ............... 23/253 R; 23/253 A; 23/259; 195/127; 235/151.12; 235/151.35
[51] Int. Cl.² ..................... G01N 27/52; G01N 1/14
[58] Field of Search .......... 23/253 R, 253 A, 230 B, 23/230 A, 259; 195/127; 235/151.12, 151.35

[56] References Cited
UNITED STATES PATENTS

| | | | |
|---|---|---|---|
| 3,591,480 | 7/1971 | Neff et al. | 23/230 |
| 3,791,793 | 2/1974 | Friedmann et al. | 23/230 A |
| 3,857,771 | 12/1974 | Sternberg | 23/253 R |

Primary Examiner—R. E. Serwin
Attorney, Agent, or Firm—Raymond F. MacKay

[57] ABSTRACT

An auto-ranging glucose measuring system including a device capable of mixing a glucose containing solution and a diluent in a variable ratio, a glucose oxidase enzyme converter column for converting the diluted glucose solution to hydrogen peroxide as one of the products, an amperometric detector for producing an analog electric signal proportional to the concentration of hydrogen peroxide, a high-low limit circuit for producing a pulse output when the analog electric signal is greater than the preset high limit of the linear span of the detector or is less than the preset low limit of the noise level of the detector, an electronic motor speed changing circuit interposed between a source of alternating current and a pump motor in said mixing device, having a frequency dividing network controllable by a register whose contents may be incremented or decremented by a pulse from the high-low limit circuit.

12 Claims, 4 Drawing Figures

AUTO-RANGING GLUCOSE MEASURING SYSTEM

BACKGROUND OF THE INVENTION

1. Field of the Invention

This invention is related to a continuous glucose concentration measuring system wherein the glucose containing sample flows continuously through a glucose oxidase enzyme converter column producing hydrogen peroxide as one of the products which is measured by an amperometric detector producing an analog electric signal proportional to the concentration of glucose in the original sample.

2. The Prior Art

Prior art continuous glucose concentration measuring systems for solutions requiring dilution provided for manually setting the dilution ratio of the glucose containing sample and the diluent to obtain an analog electric output signal from the amperometric detector within its linear output capability and above its noise level.

SUMMARY OF THE INVENTION

A system for measuring a characteristic of a solution in which the relationship between a measured variable and a characteristic of a solution includes a linear portion and a non-linear portion and in which it is desired to have the measurement occur within said linear portion despite wide variations in the characteristic of said solution; modifying means having an input to receive said solution for modifying the characteristic of said solution, measuring means coupled to the output of said modifying means for producing a measured variable in the form of an electric signal output responsive to the characteristic of said modified solution having a settable upper limit device and a settable lower limit device related to said electrical signal, the difference between said upper and lower limits defines a useable span of said measuring means corresponding to said linear portion of said relationship; and means responsive to said upper and lower limit devices to vary said modifying means to maintain said electric signal within said linear portion of said relationship whereby the magnitude of said characteristic of said solution throughout a wide range may be determined jointly from said measuring means and said modifying means.

In a more specific embodiment, an auto-ranging measuring system of the continuous type for determining the concentration of glucose in a solution includes a sampling device for obtaining a glucose containing solution from a source of liquid containing glucose, a source of diluent, dilutor means for combining said glucose containing solution and said diluent in a predetermined dilution ratio, converter means for converting the diluted glucose containing solution from said dilutor means into hydrogen peroxide as one of the products, detector means responsive to said hydrogen peroxide for producing an analog electric signal indicative of the glucose concentration in said diluted glucose containing solution, a high-low limit means for producing an output pulse when said analog electric signal is greater than a preset high limit or is less than a preset low limit, and control means responsive to the output pulse from said high-low limit means and coupled to said dilutor means to alter said predetermined dilution ratio by increasing said ratio in response to a high limit pulse and decreasing said ratio in response to a low limit pulse, whereby the analog electric output signal from said detector means is maintained between said high limit and said low limit and the glucose concentration in said solution is determined jointly from said analog electric signal and said dilution ratio.

DETAILED DESCRIPTION OF THE PREFERRED EMBODIMENTS

Figure 1:
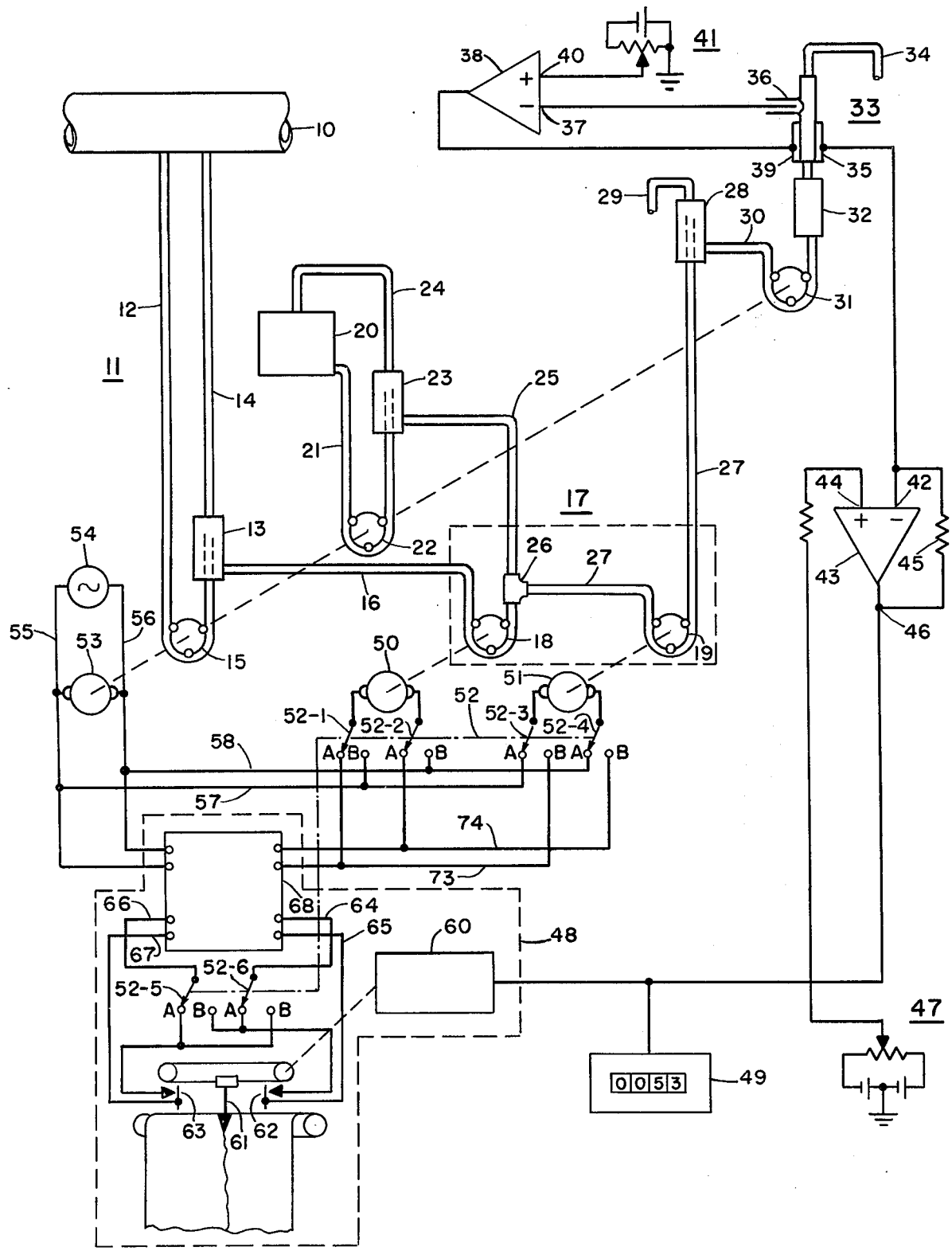
FIG. 1 schematically shows in block diagram an overall glucose measuring system utilizing the invention.

In FIG. 1 a fluid sampler 11 draws a glucose containing solution from a fluid conduit 10. The fluid sampler 11 may be a pipe or tubing loop as shown in FIG. 1, consisting of a tubing 12, a debubbler or gas separator 13 and a tubing 14. One end of tubing 12 is connected to fluid conduit 10 while the other end of tubing 12 is connected through the lower end of debubbler 13 to a point slightly below the top of debubbler 13. Debubbler 13 is a completely enclosed unit of cylindrical shape. One end of tubing 14 is connected to the top of debubbler 13 while the other end of tubing 14 is connected to the fluid conduit 10. Glucose containing solution is drawn from conduit 10 through tubing 12 by looping tubing 12 over peristaltic pump head 15. In some cases, the tubing around the peristaltic pump may consist of a separate piece of tubing. The amount of glucose containing solution drawn through tubing 12 depends on the inside diameter of tubing 12 and the speed of rotation of peristaltic pump head 15. The glucose containing solution entering debubbler 13 by way of tubing 12 completely fills the debubbler 13 driving all air and gases out through tubing 14 in a continuous flow with the glucose containing solution back into fluid conduit 10.

At or near the bottom of debubbler 13, there is connected a tubing 16 for conducting bubble-free glucose containing solution into a fluid dilutor 17. The dilutor 17 consists of a first peristaltic pump head 18, a second peristaltic pump head 19 and a source of diluent containing a buffer of predetermined pH, which may be in any suitable container 20. At or near the bottom of the container 20, there is connected a tubing 21 for conducting the diluent around a peristaltic pump head 22 and thence to a debubbler 23 through its lower end to a point slightly below the top of debubbler 23. The construction of debubbler 23 is identical to that of debubbler 13. The pump head 22 is also identical to that of pump head 15 and they generally are secured to the same drive shaft. In some cases a single pump head of wider construction may be used to accommodate both tubings 12 and 21. A tubing 24 connects the top of debubbler 23 to the top of container 20 for conducting the unused diluent with any gas or air bubbles back into container 20.

At or near the bottom of debubbler 23, there is connected a tubing 25 for conducting bubble-free diluent to be mixed with bubble-free glucose containing solution through tubing 16. The tubing 16 is looped around peristaltic pump head 18 for establishing a predetermined flow rate in tubing 16 for the bubble-free glucose containing solution. Both tubings 16 and 25 are joined together by way of a T-fitting 26 and to a tubing 27 which loops around the peristaltic pump head 19 for establishing a predetermined flow rate for the mixture of glucose containing solution and diluent.

In a specific example tubings 16, 25 and 27 are of silicone rubber having 0.105, 0.170, 0.170 inch of outside diameter and 0.040, 0.110, 0.110 inch of inside diameter respectively. Of course they may be of any convenient size, such as 1/16 inch inside diameter. The respective flow rates through tubing 16 and 27 at a pump speed of 12 r.p.m. for both pumps 18 and 19 are 0.5 ml./min. and 5.0 ml./min. Since there is 0.5 ml./min. of glucose containing solution flowing through tubing 16 towards T-fitting 26 and 5.0 ml./min. flowing through tubing 27 away from T-fitting 26, there must be 4.5 ml./min. of diluent flowing through tubing 25. Hence the dilution ratio is 5.0/0.5 or 10:1 as stated by chemists. The dilution ratio may be changed by changing the speed of either or both pumps 18 and 19. An increase in the speed of pump 18 would provide more glucose containing solution flowing through tubing 16, and hence the dilution ratio will be reduced. A reduction in dilution ratio can also be accomplished by decreasing the speed of pump 19 thus reducing the flow through tubing 27 which in turn causes a reduction of diluent flow through tubing 25.

The outlet from dilutor 17 through tubing 27 is connected to a third debubbler 28 having over-flow discharge port 29. At or near the bottom of debubbler 28 there is connected a tubing 30 which loops around a peristaltic pump head 31 for conducting bubble-free diluted glucose containing solution at a predetermined constant flow rate into an enzyme reaction converter column 32 for specifically converting glucose into hydrogen peroxide as one of the products. From column 32, the hydrogen peroxide containing solution flows through an amperometric detector 33 and thence into a waste discharge port 34.

A suitable amperometric detector 33 is more fully described in co-pending application Ser. No. 383,855 filed July 30, 1973 in the name of H. W. Levin, a co-worker, now U.S. Pat. No. 3,902,970, and Ser. No. 469,141 filed May 10, 1974 in the names of one of the present inventors, G. R. Moreland, and V. S. Underkoffler and J. G. Connery, co-workers, now U.S. Pat. No. 3,917,524. Briefly, it consists of a measuring electrode 35, an Ag-AgCl reference electrode 36 and a counter electrode 39. All of these three electrodes are in electrical contact with the hydrogen peroxide containing solution. A suitable d.c. potential is applied between measuring electrode 35 and counter electrode 39 for converting the hydrogen peroxide into water and oxygen. This is accomplished by an operational amplifier 38 having its inverting input 37 connected to reference electrode 36, its output connected to counter electrode 39 and its non-inverting input 40 connected to a source of adjustable potential 41. In a typical set-up source 41 is adjusted to apply 0.85 volts to input 40 to produce 0.85 to 0.9 volts at counter electrode 30 so that hydrogen peroxide passing between counter electrode 39 and measuring electrode 35 will be reduced to produce hydrogen ion and gaseous oxygen.

Measuring electrode 35 is maintained at substantially ground or circuit common potential by a connection to the inverting input 42 of another operational amplifier 43 whose non-inverting input 44 is connected to a source of adjustable current 47. When no hydrogen peroxide is flowing between electrode 39 and 35, there is still a residual current flowing from measuring electrode 35 to input 42. Source 47 provides for a means to adjust for zero signal at output 46 when there is no hydrogen peroxide flowing. Because of the feedback resistor 45 connected to operational amplifier 43, the current flowing from the measuring electrode 35 to input 42, is converted into a voltage at the output 46 of operational amplifier 43 of magnitude proportional to the current flowing from the measuring electrode 35 into input 42 and hence also proportional to the hydrogen peroxide flowing between electrodes 39 and 35. The output voltage signal at the output 46 is connected to a feedback or control circuit 48 including limit means and to a digital readout and display apparatus 49, such as is described in U.S. Pat. No. 3,686,665 issued to L. F. Elias and J. H. Magee and assigned to the assignee of this application. From the foregoing description it follows that the concentration of glucose in the original solution is equal to the readout on display apparatus 49 divided by the dilution ratio.

The output of controller 48 is alternatively connected to control either a motor 50 which is mechanically coupled to drive peristaltic pump 18 or to a motor 51 which is mechanically coupled to drive peristaltic pump 19. The motors 50 and 51 are of the type that may be energized either from an A.C. power supply or from a source of pulses. Such motors are commercially available from Sigma Instruments Inc. and are referred to as Cyclone Stepping Motors. The selection of either the A.C. source or the output from controller 48 may be readily made by switching contacts 52-1 to 52-4 of a 6-pole double-throw switch 52. The other peristaltic pumps 15, 22 and 31 are preferably driven at a constant speed by mechanical coupling to motor 53 energized by a suitable source of alternating current 54 electrically connected by conductors 55, 56 to motor 53. With the switch 52 in position A as shown, the speed of motor 50 is controlled by the controller 48 by way of electrical conductors 73, 74 and motor 51 is connected by way of conductors 55, 57 and 56, 58 to be energized by the source of alternating current 54 for constant speed operation. With the switch 52 in the B position (not shown) the speed of motor 51 is controlled by controller 48 by way of electrical conductors 73, 74 and motor 50 by way of conductors 55, 57 and 56, 58 is energized by the source of alternating current 54 for constant speed operation.

Controller 48 includes a servo positioning circuit 60 which may be of any suitable type such as that disclosed in U.S. Pat. Nos. 2,846,629 and 3,697,871. This servo positioning circuit 60 positions an indicator-pen assembly 61 of a strip chart recorder. When the measured signal from output 46 of operational amplifier 43 exceeds a predetermined high limit, the servo positioning circuit 60 positions the indicator-pen assembly 61 to close a switch 62 thereby producing a closed circuit at terminals 64 and 65 by way of switching contact 52-6 in the A position. Similarly, when the output at 46 of operational amplifier 43 is below a predetermined low limit, the servo positioning circuit will position the indicator-pen 60 to close switch 63 thereby providing a closed circuit at terminals 66 and 67 by way of switching contact 52-5 in the A position.

Figure 3:
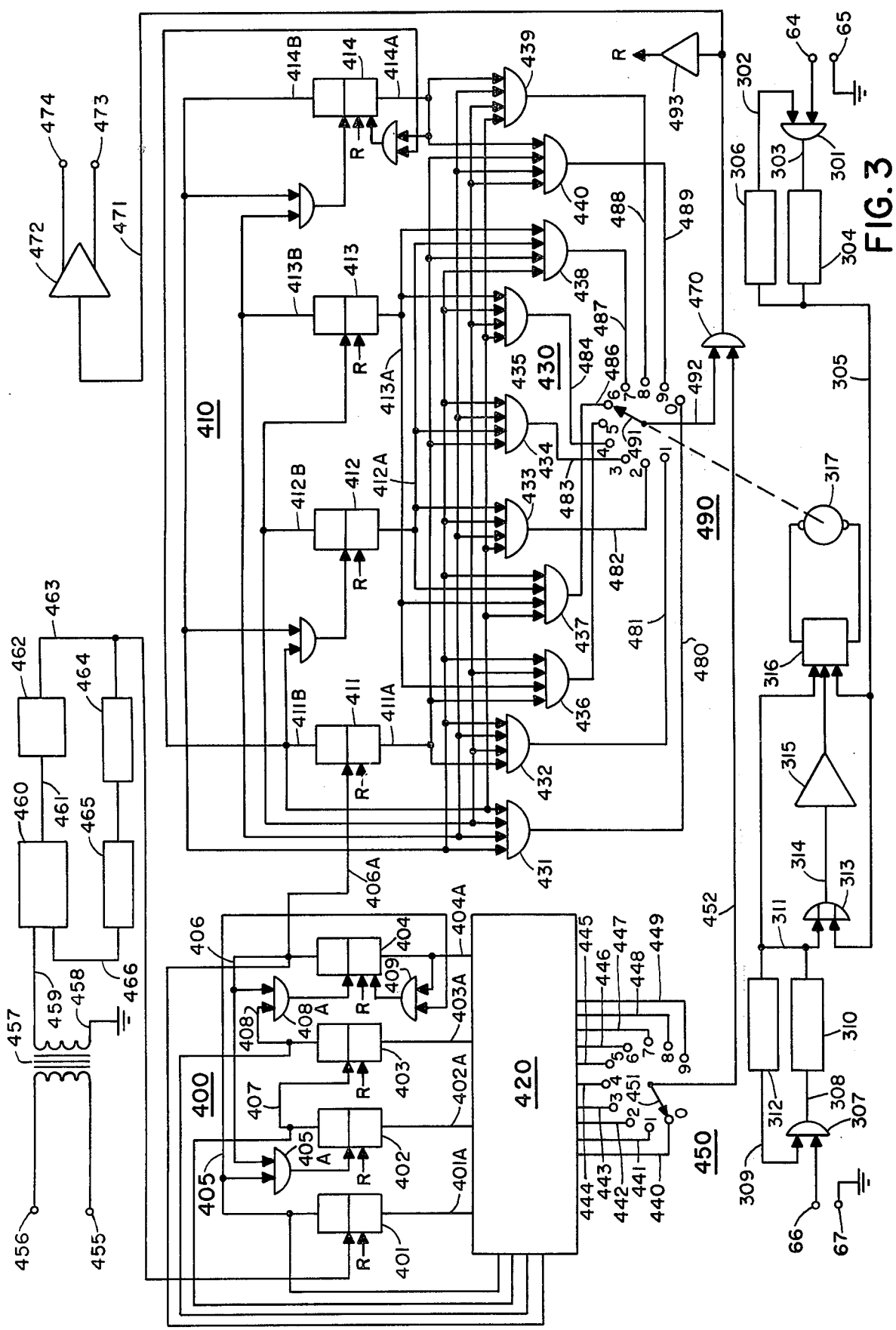
FIG. 3 shows the motor control circuit for the dilutor of FIG. 1 in greater detail.

Near the bottom of FIG. 3 there is shown the terminals 64, 65 and 66, 67 corresponding to the terminals of the same numbers of control circuit 68 in FIG. 1. Assuming there has not been a previous signal that exceeded either the high limit or the low limit for some period of time, an AND gate 301 has an enabling signal level on lead 302 as one of its two inputs. The closing of high limit contact 62 in FIG. 1 and switching contact 52-6 in its A position corresponds to a closed circuit connection between terminals 64 and 65 producing the other signal input to AND gate 301, thus, producing an output from that AND gate on lead 303 connected as an input to a short delay device or single shot 304. The output of the single shot 304 is a narrow pulse on line 305 that is applied as an input signal to a long delay circuit or single shot 306. The single shot 306 in response to the narrow pulse applied to its input produces a long pulse on line 302 which serves as an inhibit signal venting any pulse signal applied through AND gate 301 from again triggering single shot 304 for the duration of the long pulse. The duration of delay for delay circuit 306 is selected to be greater than the response time of the measuring system under consideration. That response time is the time it takes for the amperometric cell 33 of FIG. 1 to fully change the signal from measuring electrode 35 for a step change in glucose level in tubing 27 or in the main conduit 10. Single shot 304 and long delay circuit 306 are similar to FIG. 15.84 on page 15–56 of HANDBOOK OF SEMICONDUCTOR ELECTRONICS by Lloyd P. Hunter, 3rd Edition, McGraw-Hill Book Company.

Similarly, when the low limit contact 63 is closed and switching contact 52-5 in its A position, it provides a closed circuit between terminals 66 and 67 producing an input to AND gate 307 and producing an output on line 308, provided the other input on line 309 to AND gate 307 is enabled. With a signal on line 308 passing through a short delay circuit or single shot 310, there is produced a narrow output pulse on line 311 and also as an input to long delay circuit 312 whose output produces an inhibit signal on line 309 to prevent further signals passing through AND gate 307.

Both lines 305 and 311 are connected to apply pulses to an OR gate 313 whose pulse output on line 314 is amplified by an amplifier 315 and thence applied to a stepping motor control circuit 316 to control a stepping motor 317. The stepping motor control circuit 316 also has an input from line 305 and an input from line 311 to indicate the direction that the stepping motor should be stepped in response to a pulse signal from amplifier 315. The stepping motor 317 is shown mechanically coupled to a decade selector switch 490.

At the top of FIG. 3, terminals 455 and 456 are respectively connected to conductors 55 and 56 of FIG. 1 to a source of alternating current 54. Terminals 455 and 456 are also connected to the primary winding of an isolating transformer 457. The secondary winding of that transformer is connected at one end to circuit common at 458 and at the other end to a conductor 459. The conductor 459 is connected to one of the inputs of a phase-frequency detector or comparator 460 (such as MC 4344/4044 manufactured by Motorola Inc.). The output of this comparator by way of conductor 461 is applied to a pulse generator voltage controlled oscillator 462 (such as MC 1648 or MC 4324/4024 manufactured by Motorola Inc.). The output of this oscillator is in the form of pulses predetermined to have a repetition frequency several decades higher in frequency than the source of alternating current, source 54, for instance, it may be 100 times higher in frequency or 6,000 Hz. The pulse output of pulse generator 462 by way of line 463 is applied to 2 decade counters 464 and 465 in cascade dividing the oscillator frequency by 100. Thus, the output of the second decade counter 465 by way of conductor 466 is applied as the other input to comparator 460. If there are discrepancies between the frequency or phase of the signals on lines 459 and 466, the comparator 460 changes the voltage signal on line 461 to change the pulse repetition frequency of pulse generator 462 in a direction to minimize the differences between the signals on lines 459 and 466. A detailed description appears in "Phase-Locked Loop Data Book," 2nd Edition August 1973 by Motorola Inc. The decade counters 464 and 465 may be those described in that book, such as MC 54/74416 manufactured by Motorola Inc. or similar to the decade counters to be described.

The pulses from pulse generator 462 on line 463 are applied to the input of a decade counter 400. The decade counter 400 consists of four flip-flop stages, 401, 402, 403 and 404. For the purposes of illustration the 1-2-4-8 binary coded decimal code will be used. Therefore, flip-flop 401 will produce a signal representative of a 1 on line 401A, flip-flop 402, representative of a 2 on line 402A, flip-flop 403, representative of a 4 on line 403A, and flip-flop representative of an 8 on line 404A. The application of a reset signal R to all of the flip-flop stages of counter 400 will render the lower half of each flip-flop stage conductive or in a "low" potential state and hence no output signal on lines 401A-404A. The first pulse on conductor 463 changes the state of flip-flop 401 resulting in its lower half becoming non-conductive or in a "high" potential state representative of a 1 on line 401A. The second pulse on conductor 463 changes the state of flip-flop 401 again. The signal level on conductor 405 changes from "low" to "high" level as an input to AND gate 405A and the signal on conductor 401A changes to its "low" level. In conjunction with the enabling "high" level signal from flip-flop 404 via conductor 406 as the other input to AND gate 405A there is produced a changing output level applied to the input to flip-flop 402 which in turn produces a "high" level output on line 402A representative of a 2. The third pulse arriving via line 463 to flip-flop 401 produces a high level output on line 401A representative of a 1. It is to be noted that the output on line 402A is still present. Thus, there is a signal on both lines 401A and 402A representing a 1 and a 2, respectively, making a total of 3. The fourth pulse arriving via conductor 463 to flip-flop 401 again changes the state of flip-flop 401 producing a "low" level signal on conductor 401A and producing a change in signal level on conductor 405 from "low" to "high" which by way of enabled AND gate 405A changes the state of flip-flop 402 to produce a low level signal on conductor 402A and a high level signal on conductor 407 to flip-flop 403 which in turn changes the state of flip-flop 403 to produce a "high" level produces output on conductor 403A representative of a 4. The fifth pulse arriving via conductor 463 produces an output on conductor 401A representative of a 1. The signal representative of a 4 on conductor 403A is also present making a total of 5. The sixth pulse arriving via conductor 463 removes the "high" level signal on conductor 401A and produces a "high" level signal on conductor 405 and by way of enabled AND gate 405A produces a "high" level output on conductor 402A representative of a 2. Again the "high" level signal on conductor 403A is still present making a total representation of 6. The seventh pulse arriving via conductor 463 produces a "high" level output on conductor 401A representative of a 1 which with "high" level the signal on conductor 402A representative of a 2, and the high level signal on conductor 403A which is representative of a 4 provides output signals from counter 400 representing the count of 7. The eighth pulse arriving at conductor 463 removes the "high" level signal from conductor 401A and produces a "high" level signal on conductor 405 through enabled gate 405A, to remove the "high" level signal from conductor 402A and produce a signal on conductor 407 which in turn removes a signal on conductor 403A and produce a "high" level signal on conductor 408 as an input to AND gate 408A which is enabled by the "high" level signal on conductor 406. The resulting change to a "high" level in the output of gate 408A is supplied to flip-flop 404 to produce a "high" level output on line 404A representative of an 8. It is to be noted that the "high" level signal appearing on conductor 404A is accompanied by removal of the "high" level signal on conductor 406 which was the enabling signal to AND gates 405A and 408A. When the ninth pulse arrives via conductor 463 it produces a "high" level output on conductor 401A representative of a 1 which with the "high" level signal on conductor 404A is representative of an 8 provides a total count of 9. When the tenth pulse arrives on conductor 463, it removes the "high" level signal on conductor 401A, produces a change from a "low" to a "high" level signal on conductor 405 as an input to AND gate 409. Gate 409 had been enabled by the "high"level signal on conductor 404A and resets the flip-flop 404, removing the high level signal on conductor 404A resulting in a "low" level signal on all of the conductors 401A-404A representing a zero count. The resetting of flip-flop 404 also produces a "high" level signal on conductor 406A as an input to flip-flop 411 of decade counter 410. Decade counter 410 is identical with counter 400 having decade stages 411, 412, 413 and 414 and the operation of decade counter 410 is identical to that of decade counter 400.

The output lines 401A-404A from decade counter 400 corresponding to output lines from flip-flops 401-404, are applied to a binary coded decimal to decimal decoder 420. The 0-9 output lines 440-449 from decoder 420 are connected to a respective contact of a decade switch 450. Similarly, the output lines 411A-414A from decade counter 410 corresponding to output lines from flip-flops 411-414, are applied to a binary coded decimal to decimal decoder 430. The 0–9 output lines 480–489 from decoder 430 are connected to a respective contact of a decade switch 490. Decoders 420 and 430 are identical and only decoder 430 is shown in detail in FIG. 3 and its operation will now be described.

Decoder 430 consists of AND gates 431–440, each having an output line 480–489 respectively. Each of these AND gates 431–440 has four input lines. Each of the four inputs of AND gate 431 is connected to output lines 411B-414B on which a high level signal corresponds to the zero state of flip-flops 411–414. When each of the flip-flops 401–404 and 411–414 are in its zero state represented by a "low" level signal output on lines 401A-404A and 411A-414A, all of the lines 411B-414B produce a "high" level signal that are applied to AND gate 431 producing a "high" level output on line 480 connected to the 0 (zero) contact of decade selector switch 490. Each of the AND gates 432-439 have at least one of their inputs receiving a "low" level signal from flip-flops 411-414 so that the outputs from those gates are all at their "low" level.

AND gate 432 having its output on line 481 connected to the 1 (one) contact of decade selector switch 490, has one input connected to line 411A from flip-flop 411 and its other three inputs connected to lines 412B, 413B and 414B. Similarly, AND gate 433 has its output on line 482 connected to the 2 (two) contact of decade selector switch 490, one of its inputs connected to line 412A and its other three inputs connected to line 411B, 413B and 414B. However, AND gate 434 having its output on line 483 connected to the 3 (three) contact of decade selector switch 490, has one input connected to line 411A, another input connected to line 412A and the other two inputs to lines 413B and 414B.

AND gate 435 having its output on line 484 connected to the 4 (four) contact of decade selector switch 490, has one input connected to line 413A from flip-flop 413 and its other three inputs connected to lines 411B, 412B and 414B. While, AND gate 436 having its output on line 485 connected to the 5 (five) contact of switch 490, has an input connected to line 413A, another input connected to line 411A and its other two inputs connected to lines 412B and 414B; AND gate 437 having its output on line 486 connected to the 6 (six) contact of switch 490, has an input connected to line 413A, another input connected to line 412A its other two inputs connected to lines 411B and 414B; and AND gate 438 having its output on line 487 connected to the 7 (seven) contact of switch 490, has three of its inputs connected to lines 411A, 412A and 413A and its fourth input connected to line 414B.

AND gate 439 having its output on line 488 connected to the 8 (eight) contact of decade selector switch 490, has one input connected to line 414A and its other three inputs connected to lines 411B, 412B and 413B; and AND gate 440 having its output on line 489 connected to the 9 (nine) contact of decade selector switch 490, has an input connected to line 411A, another input connected to line 414A and its other two inputs connected to lines 412B and 413B.

The rotor contacts 451, 491 of decade selector switches 450 and 490, are connected by way of conductors 452, 492 to the two inputs of AND gate 470 whose output appears on line 471 to be amplified by amplifier 472 and appears at amplifier output terminals 473, 474 which are connected to conductors 73 and 74 respectively in FIG. 1. At the start-up of the measuring system, the contact 491 may be in its extreme clockwise 0 position or any of the positions 1 to 9. When contacts 451, 491 are in their 0 positions, each of counters 400, 410 becomes a decade counter equivalent to decade counters 464 and 465, and hence there will be 60 pulses per second flowing through AND gate 470.

Since there is a finite time of response of the measuring system of about 2 minutes for each change in dilution ratio, a closer estimate of the final setting of rotor contact 491 would shorten the time required for auto ranging of the measuring system. Assuming contact 491 is set at 5 and contact 451 is set at 0, then every 50th pulse passes through AND gate 470 to amplifier 472 and to amplifier 493 producing a reset-signal R applied to flip-flops 401-404 and 411-414 to start the count of pulses from pulse generator 462 over again. The repetition rate will be 6,000/50 or 120 pulses per second. If the output of the amperometric detector appearing at output 46 of amplifier 43 (FIG. 1) is now above the predetermined upper limit as indicated by the closing of switch contact 62, and switching contact 52-6 is in its A position a pulse is produced to step stepping motor 317 by way of AND gate 301, single-shot 304, conductor 305, OR gate 313, amplifier 315 and motor control circuit 316. Motor control circuit directs the rotation of the stepping motor 317 and in this case the motor 317 will step the rotor contact 491 to position 6, allowing 6,000/60 or 100 pulses per second to pass through AND gate 470 for increasing the dilution ratio. On the other hand, if the output of the amperometric detector appearing at output 46 is below the predetermined lower limit as indicated by the closing of switch contact 63 and switching contact 52-5 is in its A position, the stepping motor 317 will step rotor contact 491 to a lower 4 position, allowing 6,000/40 or 150 pulses per second to pass through AND gate 470 for decreasing the dilution ratio because flow in tubing 16 increases and flow in tubing 25 decreases.

The foregoing description demonstrates the tendency of the auto-ranging measuring system to bring the glucose derived hydrogen peroxide concentration for the amperometric detector to be between the high and low limit of its linear range when switch 52 is in the A position as shown in FIG. 1. If switch 52 is in the B position, motor control circuit 316 will have to direct the stepping motor 317 in the opposite direction. More particularly, if the output of the amperometric detector appearing at output 46 of amplifier 43 is above the upper limit as selected by the closing of switch contact 62 (and switching contact 52-5 is in its B position) producing a pulse to step stepping motor 317 and rotor contact 491 to position 4 allowing 6,000/40 or 150 pulses per second to pass through AND gate 470 for increasing the dilution ratio. In like manner, if the output of the amperometric detector appear at output 46 is below the lower limit as selected by the closing of switch contact 63 (and switching contact 52-6 is in its B position) producing a pulse to step stepping motor 317 and rotor contact 491 to position 6 allowing 6,000/60 or 100 pulses per second to pass through AND gate 470 for decreasing the dilution ratio because of the constant flow through tubing 16 and increased flow through tubing 25.

From the foregoing description, it can be appreciated that the combination of counter 410 and decoder 430 may be replaced by an up-down decade ring counter, such as ring counters described in U.S. Pat. No. 3,592,045 assigned to the assignee of the instant patent application. Similarly, the function of counter 400 and decoder 420 may also be replaced by an up-down ring counter.

Each of the decade selector switches 450, 490 performs the function of a settable co-incidence gate and each ten-position switch may be replaced by ten co-incidence AND gates, each of these gates having an input connected to one of the lines 440–449 or 480–489 and having another input connected to a respective output line of an up-down decade ring counter. Each of the two up-down decade ring counters may be manually set by manually adding one or more pulses to its count up or count down input. In addition the up-down decade ring counter whose output is connected to the coincidence gates replacing switch 490 will have its count up input connected to line 305 and its count down input connected to line 311 when switch 52 (FIG. 1) is in the A position; or its count up input may be connected to line 311 and its count down input may be connected to line 305 if switch 52 is in the B position.

Figure 4:
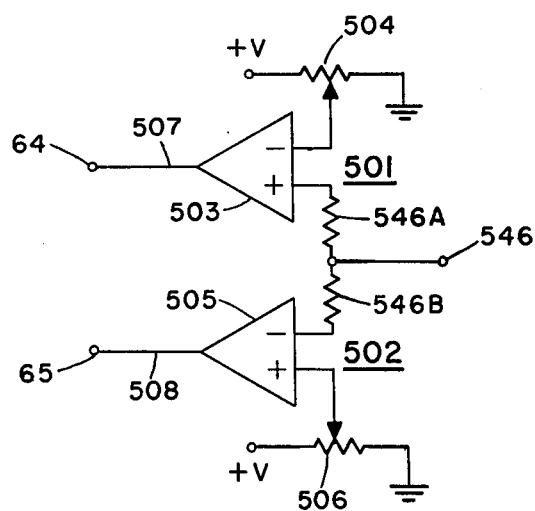
FIG. 4 shows details of an alternative high-low limit circuit useful in the system of FIG. 1.

In a fast response measuring system, the servo-positioning circuit 60, its associated indicator 61, and contacts 62, 63 of FIG. 1 may be replaced by limit amplifiers as shown in FIG. 4. This may be especially desirable when there is no need for our analog record and only a linearized digital readout from readout and display apparatus 49 is desired.

In FIG. 4 the terminal 546 is connected to conductor 46A (in FIG. 1). Terminal 546 is connected a high limit circuit 501 and a low limit circuit 502. A resistor 546A couples the terminal 546 to the non-inverting input of an operational amplifier 503. The inverting input of operational amplifier 503 is connected to a source of an adjustable bias having a potentiometer 504. A resistor 546B is coupled between the terminal 546 and the inverting input of another operational amplifier 505. The non-inverting input of operational amplifier 505 is connected to a source of adjustable bias having a potentiometer 506. The output of operational amplifier 503 by way of conductor 507 is connected to terminal 64 of FIG. 4. Similarly, the output of operational amplifier 505 by way of conductor 508 is connected to terminal 66 of FIG. 3. The amplifier 503 and 505 have a high gain and the output is normally at either a positive or negative saturation level and changes from one to the other for very small changes in the input signal level.

With such an amplifier characteristic for amplifiers 503 and 505 the circuit shown in FIG. 4 performs the same function as the servo-positioning circuit 60 and limit contacts 62 and 63 it replaced. Assume potentiometers 504 and 506 are set to correspond to the high limit switch 62 and low limit switch 63 positions respectively, i.e. the potential on conductor 46A to close either of switches 62 and 63 is the same as for the output on either of conductors 507, 508 to change from minus (+) to plus (−) abruptly. When the signal on conductor 46A is within the two limit conditions, the output of amplifier 503 on conductor 507 is a negative potential determined by the setting of potentiometer 504 variable contact which is a positive potential applied to the inverting input of amplifier 503. Similarly, the output of amplifier 505 on conductor 508 is a negative potential determined by the setting of potential motor 506 variable contact which is a positive potential applied to the non-inverting input of amplifier 505. When the potential on conductor 46A exceeds the potential set by potentiometer 504, the output potential of amplifier 503 on conductor 507 will change from negative to positive to produce an output signal from AND gate 301. When the potential on conductor 46A decreases below the potential set by potentiometer 506, the output potential of amplifier 505 on conductor 508 will change from negative to positive to produce an output signal from AND gate 307.

Figure 2:
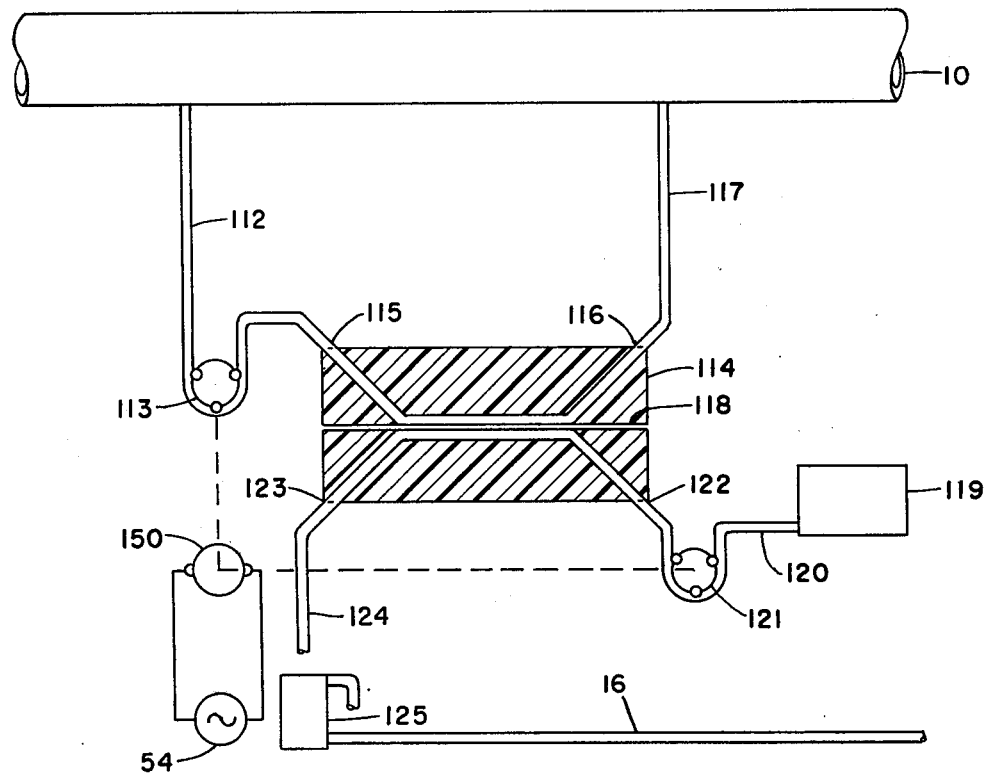
FIG. 2 shows in more detail a fluid sampler that is useful in the system of FIG. 1.

An alternative fluid sampler that may be used in place of the fluid sampler 11 shown in FIG. 1 is shown in FIG. 2. Similar to FIG. 1, there is a circulating fluid path through tube 112, pump 113, glucose exchange device 114 and tube 117 which circulates fluid from and back to a conduit 10 through which flows a solution containing glucose. The fluid is pumped through the tube 112 by way of a peristaltic pump 113 into the glucose exchange device 114. The fluid path through device 114 has an entrance 115 and an exit 116. The glucose exchange device may be made of a transparent solid such as acrylic plastic which may have two identical halves separated by a membrane 118 which is selectively permeable to glucose such as a cellulose membrane available from Spectrum Medical Industries Inc., Los Angeles, Calif. as Spectrapor No. 2 having a 12,000 to 14,000 molecular weight cut-off. A source of fluid such as pure de-ionized water is stored in container 119. De-ionized water is used to prevent any possibility of contaminating the process fluid under measurement. Separation of the process fluid from the measuring system fluid by the membrane, allows the sample in the de-ionized water to be diluted, thus effectively taking the place of a stage of dilution. This in turn reduces the transit time and thereby reduces the time of response of the measuring system.

Returning to FIG. 2, at the bottom of container 119 there is a tube 120 for flow of the de-ionized water in the tube 120 by way of peristaltic pump 121 into the glucose exchange device 114 at entrance 122 and flowing past the membrane 118 to exit 123. The solution then flows through pipe 124 into a collecting device 125. It can be seen in FIG. 2 that the glucose-containing fluid enters the glucose exchange device 114 by an inlet 115 passing by membrane 118 and out through exit 116, while the de-ionized water enters by entrance 122 and flows by membrane 118 and through exit 123. The de-ionized water on the one side of the membrane absorbs or dissolves the glucose permeating the membrane and carries it to the container 125. The de-ionized water containing glucose is made to drip into container 125 to remove the possibility of the de-ionized water passing through the membrane through tubing 117, into conduit 10, in case of an emergency shutdown. At the bottom of container 125 the tube 16 is the same tube 16 as shown in FIG. 1 flowing into dilutor 17. The peristaltic pumps 113, 121 may be mechanically coupled to motor 53 (FIG. 1) in a manner similar to the peristaltic pumps 15, 22 and 31 or they may be separately driven by motor 150 energized by the source 54.

The foregoing description of the invention is not to be limited to the several alternative means to practice the invention as described. It will occur to thos skilled in the art that there will be other alternative methods for practice of this invention within the spirit of the invention as defined more succinctly in the appended claims.

What we claim is:

1. A system for measuring a characteristic of a solution in which the relationship between a measured variable and the characteristic includes linear and non-linear portions and in which it is desired that the measurement occur in said linear portion comprising:

a source of said solution the characteristic of which is to be measured, modifying means having an inlet to receive said solution for modifying the characteristic of said solution and an outlet, measuring means coupled to the output of said modifying means for producing an electric signal output responsive to the characteristic of said solution, a settable upper limit device for said electrical signal, a settable lower limit device for said electric signal, the difference between said upper and lower limits defining a usable span representing said linear portion of said relationship, means responsive to said upper and lower limit devices to vary said modifying means to maintain said electric signal representative of the characteristic of said solution within said linear portion of said relation, and indicating means associated with said responsive means for indicating the extent that said characteristic is modified by said modifying means whereby the magnitude of said characteristic of said solution may be determined jointly from said measuring means and said indicating means.

2. An auto-ranging continuous measuring system for determining the concentration of glucose in a glucose containing solution, comprising:

continuous sampling means for receiving said glucose containing solution, a source of diluent including a buffer solution, dilutor means coupled to said sampling means and to said source of diluent for combining said glucose containing solution and said diluent in a predetermined dilution ratio to produce a flow of diluted glucose containing solution, converter means having an inlet and an outlet, said inlet being coupled to said dilutor means for converting the glucose in said diluted glucose containing solution into hydrogen peroxide as one of the products at said outlet, detector means coupled to said oulet of said converter means and responsive to said hydrogen peroxide for producing an analog electric output signal indicative of the glucose concentration in said diluted glucose containing solution, limit means coupled to said detector means responsive to said analog electric output signal for producing a high limit signal representative of the upper limit of linearity of said analog electric signal and a low limit signal representative of the noise level in said analog electric signal, and control means coupled between said limit means and said dilutor means responsive to said high limit signal for increasing the dilution ratio of said glucose containing solution relative to said diluent and responsive to said low limit signal for decreasing the dilution ratio of said glucose containing solution relative to said diluent;

whereby said dector means analog electric output signal is maintained between said high limit and said low limit and the glucose concentration in said glucose containing solution is determined jointly from said analog electric signal and said dilution ratio.

3. The measuring system of claim 2 wherein said dilutor means comprises:

a first pump having an inlet coupled to said sampling means for continuously drawing out a portion of the glucose containing solution to be measured and an outlet, combining means having a first inlet coupled to said outlet of said first pump, a second inlet coupled to said source of diluent for combining said portion of the glucose containing solution with said diluent and having an outlet, a second pump having an inlet coupled to said outlet of said combining means and an outlet coupled to said converter means, a variable speed motor mechanically coupled to one of said first and second pumps, and electrically responsive to said limit means, and a constant speed motor connected to the other of said first and second pumps.

4. The measuring system of claim 2 wherein said limit means is comprised of high and low limit switches of a servo mechanism having its input connected to receive said analog electric output signal from said detector means.

5. The measuring system of claim 2 wherein said limit means comprises a high limit operational amplifier and a low limit operational amplifier coupled to receive said analog electric output signal from said detector means.

6. The measuring system of claim 2 wherein said limit means further comprises:
 an AND gate having two inputs and an output, one of said two inputs being coupled to said limit means to receive one of said two signals,
 a first single-shot circuit having a stable state and an active state of short duration and having an input connected to the output of said AND gate and an output, and
 a second single-shot circuit having a stable state and an active state of long duration and having an input connected to the output of said first single-shot circuit of short duration and an output connected to the other of said two inputs of said AND gate as an enabling signal when said single-shot circuit of long duration is in its normal state,
 whereby when said signal from said limit means passes through said enabled AND gate producing a pulse of short duration at the output of said first single-shot circuit for application to said control means, and inhibiting said AND gate for the duration of the active state of said second single-shot circuit.

7. The measuring system of claim 3 wherein said control means comprises:
 a pulse generator for producing motor operating pulses having a settable time period between pulses,
 means responsive to said limit signals connected to said pulse generator to change said settable time period, and
 said variable speed motor comprises a stepping motor electrically connected to receive said motor operating pulses and mechanically coupled to one of said first and second pumps to vary said dilution.

8. The measuring system of claim 2 wherein said control means comprises:
 a pulse generator,
 an electronic decade counter for dividing the pulse rate having an input coupled to said pulse generator and ten output lines,
 a settable mechanical decade switch having a settable rotor and ten fixed terminals, each of which being respectively connected to one of the ten output lines of said electronic decade counter,
 means for electrically coupling said settable rotor to said dilutor responsive to the setting of said settable rotor to change the ratio of dilution, and
 a stepping motor mechanically coupled to said settable rotor and electrically coupled to said limit means for receiving said high limit signal and said low limit signal.

9. The measuring system of claim 2 wherein said glucose containing solution is flowing in a stream, and
 said sampling means includes a circulating glucose containing solution path and a circulation pump having an inlet connected to an up-stream point of said stream and
 having an outlet connected to a down-stream point of said stream.

10. The measuring system of claim 9 wherein said circulating glucose containing solution passes by one side of a membrane pervious to said glucose solution, and another source of diluent of distilled de-ionized water passing by the other side of said membrane for transfer of glucose through said membrane into said de-ionized water.

11. An auto-ranging glucose solution measuring system, comprising:
 a sampling means for receiving said glucose solution,
 a source of diluent including a buffer solution for maintaining a pH between 5 and 8,
 dilutor means coupled to said sampling means and to said source of diluent for producing a diluted glucose solution, including a variable speed, motor driven, peristaltic pump for changing the dilution ratio,
 a glucose oxidase enzyme converter column coupled to said dilutor means for converting said diluted glucose solution into hydrogen peroxide as one of the products on conversion,
 an amperometric detector coupled to said converter column responsive to said hydrogen peroxide for producing an analog electric output signal proportional to the concentration of said hydrogen peroxide,
 a high limit circuit coupled to said amperometric detector and responsive to said analog electric signal for producing output pulses of short duration when said analog electric signal has exceeded a predetermined high limit, each of said short pulses being separated by a duration substantially equal to the response time of said measuring system,
 a low limit circuit coupled to said amperometric detector and responsive to said analog electric signal for producing output pulses of short duration when said analog electric signal is less than a predetermined low limit, each of said short pulses being separated by a duration substantially equal to the response time of said measuring system,
 a pulse generator,
 a pulse count divider coupled to said pulse generator for dividing the pulse count per unit time from said pulse generator and having a plurality of outputs, and
 selector means coupled between said pulse count divider and said variable speed motor of said dilutor for transmission of pulses to energize said variable speed motor, and responsive to said output pulse from one of said high limit and low limit circuits for selecting one of said plurality of outputs from said pulse count divider to said variable speed motor to change the dilution ratio of said dilutor by changing the speed of such motor.

12. In a continuous glucose solution concentration measuring system, an improved dilutor comprising:
 a source of glucose containing solution,
 a first pump having a positive measured output and an input connected to said source of glucose containing solution to supply a measured quantity of a glucose containing solution at its output,
 a source of diluent, a second pump having a positive measured output and an input connected to the output from said first pump and to said source of diluent, and means to operate at least one of said pumps at an adjustable speed to adjust the amount of diluent provided by said dilutor at the output of said second pump.

* * * * *